United States Patent
Hagarty

(12) 
(10) Patent No.: US 11,013,838 B2
(45) Date of Patent: May 25, 2021

(54) CLOSED LOOP SYSTEM FOR DIRECT HARVEST AND TRANSFER FOR HIGH VOLUME FAT GRAFTING

(71) Applicant: Sarah Elizabeth Hagarty, Rockford, IL (US)

(72) Inventor: Sarah Elizabeth Hagarty, Rockford, IL (US)

(73) Assignee: Sarah Elizabeth Hagarty, Rockford, IL (US)

( * ) Notice: Subject to any disclaimer, the term of this patent is extended or adjusted under 35 U.S.C. 154(b) by 1 day.

(21) Appl. No.: 16/097,077

(22) PCT Filed: Apr. 27, 2017

(86) PCT No.: PCT/US2017/029952
§ 371 (c)(1),
(2) Date: Oct. 26, 2018

(87) PCT Pub. No.: WO2017/189918
PCT Pub. Date: Nov. 2, 2017

(65) Prior Publication Data
US 2019/0105433 A1    Apr. 11, 2019

Related U.S. Application Data

(60) Provisional application No. 62/426,159, filed on Nov. 23, 2016.

(51) Int. Cl.
*A61M 1/00* (2006.01)
*A61M 39/28* (2006.01)

(52) U.S. Cl.
CPC ........ *A61M 1/0062* (2013.01); *A61M 1/0035* (2014.02); *A61M 1/0037* (2013.01); *A61M 39/28* (2013.01); *A61M 2202/08* (2013.01)

(58) Field of Classification Search
CPC ...... A61B 2018/00464; A61M 1/0062; A61M 2202/08
USPC ........................................................ 604/542
See application file for complete search history.

(56) References Cited

U.S. PATENT DOCUMENTS

| | | | |
|---|---|---|---|
| 3,487,784 A | 1/1970 | Rafferty et al. |
| 3,647,324 A | 3/1972 | Rafferty et al. |
| 4,512,726 A | 4/1985 | Strimling |
| 4,710,162 A | 12/1987 | Johnson |
| 4,969,865 A | 11/1990 | Hwang et al. |

(Continued)

FOREIGN PATENT DOCUMENTS

| | | |
|---|---|---|
| CN | 102961805 A | 3/2013 |
| CN | 103598901 A | 2/2014 |

(Continued)

OTHER PUBLICATIONS

Gabriel A, Champaneria MC, Maxwell GP. Fat grafting and breast reconstruction: tips for ensuring predictability. Gland Surg 2015;4(3):232-243. doi: 10.3978/j.issn.2227-684X.2015.04.18 (Year: 2015).*

(Continued)

*Primary Examiner* — Matthew F Desanto
(74) *Attorney, Agent, or Firm* — Benjamin Glenn; Shay Glenn, LLP

(57) ABSTRACT

A closed loop system and methods for pumping harvested fat from a patient donor site to a patient grafting site.

9 Claims, 23 Drawing Sheets

(56) References Cited

U.S. PATENT DOCUMENTS

| | | | |
|---|---|---|---|
| 5,011,380 A | | 4/1991 | Kovacs |
| 5,452,732 A | | 9/1995 | Bircoll |
| 5,472,416 A | * | 12/1995 | Blugerman .......... A61M 1/0062 604/28 |
| 5,725,545 A | | 3/1998 | Bircoll |
| 6,264,601 B1 | | 7/2001 | Jassawalla et al. |
| 6,503,450 B1 | | 1/2003 | Afzal et al. |
| 7,214,235 B2 | | 5/2007 | Bircoll |
| 7,780,649 B2 | | 8/2010 | Shippert |
| 8,066,691 B2 | | 11/2011 | Khouri |
| 8,172,832 B1 | | 5/2012 | Gonzalez |
| 8,496,702 B2 | | 7/2013 | Rigotti et al. |
| 8,622,997 B2 | | 1/2014 | Shippert |
| 8,632,498 B2 | | 1/2014 | Rimsa et al. |
| 8,771,678 B2 | | 7/2014 | Hedrick et al. |
| 9,248,384 B2 | | 2/2016 | Dominguez et al. |
| 9,278,165 B2 | | 3/2016 | Park et al. |
| 9,314,568 B2 | | 4/2016 | Gurtner et al. |
| 2004/0260232 A1 | | 12/2004 | Cimino |
| 2005/0084961 A1 | | 4/2005 | Hedrick et al. |
| 2005/0261633 A1 | | 11/2005 | Khalaj |
| 2006/0224144 A1 | * | 10/2006 | Lee ..................... A61M 1/0009 604/542 |
| 2008/0086209 A1 | | 4/2008 | Bircoll |
| 2008/0167613 A1 | * | 7/2008 | Khouri ................. A61M 1/008 604/119 |
| 2008/0177126 A1 | | 7/2008 | Tate et al. |
| 2009/0287190 A1 | * | 11/2009 | Shipper ............... A61M 1/0056 604/542 |
| 2011/0313345 A1 | | 12/2011 | Schafer |
| 2011/0319839 A1 | | 12/2011 | Del Vecchio |
| 2012/0016337 A1 | * | 1/2012 | Khalaj ................. A61M 1/0001 604/506 |
| 2012/0109747 A1 | | 5/2012 | Bircoll |
| 2013/0144211 A1 | | 6/2013 | Vogt et al. |
| 2013/0158515 A1 | | 6/2013 | Austen |
| 2013/0310748 A1 | | 11/2013 | Cheng |
| 2014/0298905 A1 | | 10/2014 | Yanai et al. |
| 2014/0338764 A1 | | 11/2014 | Wills |
| 2016/0361476 A1 | * | 12/2016 | Huang ................. C12M 45/02 |
| 2017/0028115 A1 | | 2/2017 | Muller |
| 2017/0239420 A1 | * | 8/2017 | Wells ................ A61B 17/3468 |
| 2017/0281865 A1 | * | 10/2017 | Wells ................ A61M 5/1413 |
| 2017/0312403 A1 | | 11/2017 | Hagarty |

FOREIGN PATENT DOCUMENTS

| | | |
|---|---|---|
| WO | WO88/09874 A1 | 12/1988 |
| WO | WO93/20860 A1 | 10/1993 |
| WO | WO2011/075700 A1 | 6/2011 |
| WO | WO2011/140382 A1 | 11/2011 |
| WO | WO2014/033209 A1 | 3/2014 |

OTHER PUBLICATIONS

Lee et al., The Effect of Pressure and Shear on Autologous Fat Grafting Plastic and Reconstructive Surgery, May 2013—vol. 131—Issue 5, doi: 10.1097/PRS.0b013e3182879f4a (Year: 2013).*

Gabriel et al., A Comparison of Two Fat Grafting Methods on Operating Room Efficiency and Costs, Aesthet Surg J. Feb. 2017; 37(2): 161-168, Published online Oct. 11, 2016. doi: 10.1093/asj/sjw169 (Year: 2016).*

Gir et al.; Fat grafting: Evidence-based review on autologous fat harvesting, processing, reinjection, and storage; Plastic and reconstructive surgery; 130(1); pp. 249-258; Jul. 1, 2012.

Coleman et al.; Fat grafting to the breast revisited: Safety and efficacy; Plastic and Reconstructive Surgery; 119(3); pp. 775-785; Mar. 2007.

Delay et al.; Fat injection to the breast: Technique, results and indications based on 880 procedures over 10 years; Aesthetic Surgery Journal; 29(5); pp. 360-376; Sep. 2009.

Gabriel et al.; Fat grafting and breast reconstruction: tips for ensuring predictability; Gland surgery; 4(3); p. 232-243; Jun. 2015.

Kanchwala et al.; Autologous fat grafting to the reconstructed breast: The management of acquired contour deformities; Plastic and Reconstructive Surgery; 124(2); pp. 409-418; Aug. 2009.

Khouri el al.; Diffusion and perfusion: The keys to fat grafting; PRS Global Open; 2(9):e220; 9 pages; Sep. 2014.

Khouri et al.; Megavolume autologous fat transfer: Part I. Theory and principles; Plastic and Reconstructive Surgery; 133(3); pp. 550-557; Mar. 2014.

Khouri et al.; Megavolume autologous fat transfer: Part II. Practice and techniques; Plastic and Reconstructive Surgery; 133(6); pp. 1369-1377; Jun. 2014.

Moretti, M.; Autologous fat transfer review: The Aesthetic Guide; Retreived on Jul. 8, 2016 from the internet at http://digital.miinews.com/article/Autologous+Fat+Transfer+Review/326624/32276/article.html; 6 pages; Jan. 2010.

Sinno et al.; Current thoughts on fat grafting: Using the evidence to determine fact or fiction; Plastic and Reconstructive Surgery; 137(3); pp. 818-824; Mar. 2016.

Spear et al.; Fat injection to correct contour deformities in the reconstructed breast; Plastic and reconstructive surgery; 116(5); pp. 1300-1305; Oct. 2005.

* cited by examiner

505
Infusing a fat harvesting site of a patient with a tumescence fluid using a pulsatile pump

510
Harvesting an amount of fat from the fat harvesting site into a fat collection canister

520
Connecting a first end of a tube to an outlet of the fat collection canister and a second end of the tube to a delivery cannula

530
Engaging a portion of the tube between the first end the second end with the peristaltic pump

540
Operating the pulsatile pump to draw fat from the fat collection canister through the through the delivery cannula into a fat delivery site on the patient

REVOLVE™ COLLECTION CANISTER

MESH FILTER

PROPELLER

TOP VIEW OF SYRINGE EXTRACTION

EXEMPLARY 12, 14 AND 15 GAUGE MICRO CANNULAS

PATIENT 1 2.5 MONTHS FOLLOW UP

BEFORE

LEFT OBLIQUE VIEW

FRONTAL VIEW

RIGHT OBLIQUE VIEW

AFTER

PATIENT 2 3 WEEKS POSTOP

BEFORE

LEFT OBLIQUE VIEW

FRONTAL VIEW

AFTER

PATIENT 2 failed implant, LD, radiation, here after first cycle fat grafting 400 cc and now showing effect external suction expansion.

AFTER REMOVAL OF EXTERNAL EXPANSION DEVICE

EXTERNAL EXPANSION DEVICE IN PLACE

PATIENT 2 – EFFECT OF EXTERNAL VACUUM EXPANSION

AFTER REMOVAL OF EXTERNAL EXPANSION DEVICE

BEFORE

AFTER 400 cc fat

PATIENT 3 1 MONTH FOLLOW UP

BEFORE

AFTER

FRONTAL VIEW

PATIENT 4 11.5 MONTH FOLLOW UP

LEFT OBLIQUE VIEW
BEFORE

FRONTAL VIEW

RIGHT OBLIQUE VIEW

AFTER

PATIENT 5 12 MONTH FOLLOW UP / RADIATION TO LEFT SIDE

BEFORE

RIGHT SIDE VIEW

FRONTAL VIEW

LEFT SIDE VIEW

AFTER

PATIENT CHARACTERISTICS: 15 PATIENTS, 27 BREASTS

| | MEAN | RANGE |
|---|---|---|
| Age | 53 years | 39-69 years |
| BMI | 28.5 kg/m$^2$ | 28-39 kg/m$^2$ |
| Smokers | none | none |
| Radiation | 6 of 15 patients | 7 of 27 breasts |
| Diabetes | 1 patient of 15 | 2 of 27 breasts |
| Hypertension | 5 of 15 patients | |

FIG. 21

OUTCOMES

| | MEDIAN | RANGE |
|---|---|---|
| Total Volume grafted | Total 407 cc<br>Left 271 cc  Right 125 cc | Total 200-795 cc<br>Left 125-435 cc  Right 0-360cc |
| Time to Transfer Fat | 18.5 minutes | 15-25 minutes |
| Infusion Rate | 146 cc/min | 100-250 cc/min |
| Minor Complications | 2 of 27 breasts | Erythema  Tx: oral antibiotics |
| Major Complications | 1 of 27 breasts | Pin hole in scar over implant washout/replacement |
| Follow up | 6 months | 1-18 months |

FIG. 22

FIG. 26C
RIGHT OBLIQUE VIEW
FIG. 23C
FIG. 26B
FRONTAL VIEW
FIG. 23B
FIG. 26A
LEFT OBLIQUE VIEW
FIG. 23A
PATIENT 1 8 MONTHS FOLLOW UP
BEFORE
AFTER

RIGHT OBLIQUE VIEW

FRONTAL VIEW

LEFT OBLIQUE VIEW

PATIENT 4 1 YEAR FOLLOW UP 300 CC TO LEFT, 25 CC TO RIGHT

BEFORE

AFTER

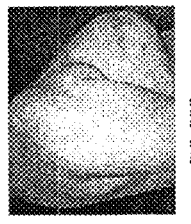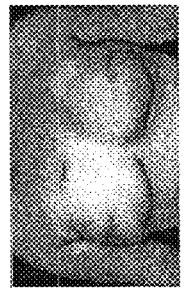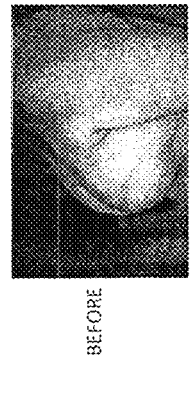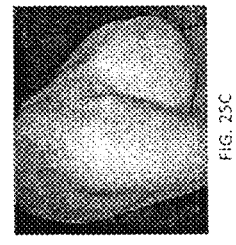
PATIENT 5 16 MONTH FOLLOW UP
BEFORE
FIG. 28A LEFT OBLIQUE VIEW
FIG. 28B FRONTAL VIEW
FIG. 28C RIGHT OBLIQUE VIEW
AFTER
FIG. 25A
FIG. 25B
FIG. 25C

CLOSED LOOP SYSTEM FOR DIRECT HARVEST AND TRANSFER FOR HIGH VOLUME FAT GRAFTING

CROSS REFERENCE TO RELATED APPLICATIONS

This application is a continuation-in-part of U.S. patent application Ser. No. 15/139,767 entitled, "A SIMPLE CLOSED LOOP SYSTEM FOR DIRECT HARVEST AND TRANSFER FOR HIGH VOLUME FAT GRAFTING" filed on Apr. 27, 2016 which is herein incorporated by reference in its entirety.

This application also claims the benefit of U.S. Provisional Patent Application No. 62/426,159, entitled "CLOSED LOOP SYSTEMS FOR DIRECT HARVEST AND TRANSFER FOR HIGH VOLUME FAT GRAFTING," filed Nov. 23, 2016, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This application related to the field of fat grafting.

BACKGROUND

Fat grafting as an adjunct for contour modulation in breast reconstruction has become fairly commonplace[1-3] since The American Society of Plastic Surgeons lifted a ban on fat grafting to the breast in 2009. Optimal methods and techniques of transfer and fat handling has become an area of increased research and technological development. Many techniques involve the transfer of fat back into the breast via a hand held 60 cc syringe powered by manual plunger. Recently, Khouri[4,5] has championed 'megavolume fat transfer' for breast reconstruction, designating mega as >300 cc per breast using this manual technique. Extrapolating this process to two breasts would necessitate at least ten 60 cc syringes. Transferring fat into syringes and refitting the plungers is tedious. Small amounts of fat may be spilt or lost with the filling of each syringe. Multiplying by ten syringes adds up to wasted viable tissue. Manually forcing the plunger after already performing manual or assisted liposuction is tiresome on the hands. What is needed are improved techniques to streamline this process, bypass the use of a syringe step, decrease operating time and anesthesia time for the patient.

SUMMARY OF THE DISCLOSURE

In general, in one embodiment, a method of performing a fat grafting process on a patient includes: (1) harvesting an amount of fat from a donor site of the patient; and (2) delivering a portion of the amount of fat into a grafting site of the patient at a rate of between 100 ml/min to 350 ml/min for at least 5 minutes.

This and other embodiments can include one or more of the following features. The method can further include delivering a second portion of the amount of fat into a second grafting site of the patient at a rate of between 10 ml/min to 150 ml/min for at least 5 minutes. The amount of fat from the harvesting step can be retained in a storage container and the delivering step can be performed by pumping the fat from the storage container directly to the grafting site. The portion of the amount of fat can be 700 cc and the delivering step is less than 22 minutes. The grafting site and the second grafting site can be on a breast. The grafting site can be on a right breast and the second grafting site can be on a left breast. The harvesting an amount can be between about 1-5 ml, 1-50 ml, 1-100 ml, 100-200 ml, 100-500 ml, 100-1000 ml or 100-2000 ml of harvested fat. Fat grafting process can be performed as part of a breast reconstruction procedure or a cosmetic breast revision procedure. Fat grafting process can be performed as part of a cosmetic body contouring procedure. The method can further include adapting a portion of the harvesting step or the delivering step to accommodate for a partial defect at the grafting site. The method can further include adapting a portion of the harvesting step or the delivering step to accommodate for a scarring from radiated tissue at the grafting site. The method can further include adapting a portion of the harvesting step or the delivering step to accommodate for an implant volume inadequacy at the grafting site.

In general, in one embodiment, a method of performing a fat grafting process on a patient includes: (1) harvesting an amount of fat from a donor site of the patient into a storage container; (2) treatment or preparation of the fat in various ways (for example centrifuging, filtering, gravitational separation, using the Revolve® system)(3) positioning a delivery cannula into a first portion of a grafting site of the patient; (4) pumping a portion of the amount of fat directly from the storage container into the first portion of the grafting site of the patient at a rate of between 100 ml/min to 350 ml/min until a first volume of fat is indicated on a pump used during the pumping step; and (5) positioning a delivery cannula into a second portion of a grafting site of the patient; and (6) pumping a second portion of the amount of fat directly from the storage container into the second portion of the grafting site of the patient at a rate of between 10 ml/min to 350 ml/min until a second volume of fat is indicated on the pump used during the pumping step, wherein the pump used during the pumping step is in continuous communication with the storage container during the positioning a delivery cannula steps.

In general, in one embodiment, a method of performing a fat grafting process on a patient includes: (1) harvesting an amount of fat from a donor site of the patient into a collection canister; (2) treatment or preparation of the fat in various ways (for example centrifuging, filtering, gravitational separation, using the Revolve® system), (3) positioning a delivery cannula into a first portion of a grafting site of the patient; (4) pumping a portion of the amount of fat directly from the collection canister into the first portion of the grafting site of the patient at a rate of between 100 ml/min to 350 ml/min until a first volume of fat is indicated by the pump used during the pumping step; and (5) positioning the delivery cannula into a second portion of a grafting site of the patient; and (6) pumping a second portion of the amount of fat directly from the collection canister into the second portion of the grafting site of the patient at a rate of between 100 ml/min to 350 ml/min until a second volume of fat is indicated by the pump used during the pumping step, wherein a single piece of tubing passes through the pump used in the pumping step and connects an outlet of the collection canister to the inlet of the delivery cannula.

These and other embodiments can include one or more of the following features. The method can further include operating the pump used in the pumping a portion steps continuously while performing the positioning the delivery cannula steps. The method can further include operating the pump used in the pumping a portion step at a first flow rate during the pumping a portion step and at a second different flow rate during the pumping a second portion step.

In general, in one embodiment, a method of performing a fat grafting process on a patient includes: (1) harvesting an amount of fat from a donor site of the patient into a storage container; (2) treatment or preparation of the fat in various ways (for example centrifuging, filtering, gravitational separation, using the Revolve® system)((3) positioning a delivery cannula into a first port of a grafting site of the patient; (4) pumping a portion of the amount of fat directly from the storage container into the first port of the grafting site of the patient until a first volume of fat is indicated on a pump used during the pumping step; and (5) positioning the delivery cannula into a second port of a grafting site of the patient; and (6) pumping a second portion of the amount of fat directly from the storage container into the second port of the grafting site of the patient until a second volume of fat is indicated on the pump used during the pumping step, wherein the pump used during the pumping step is in continuous communication with the storage container during the positioning a delivery cannula steps and the total of the first volume of fat and the second volume of fat is 150 cc or less.

In general, in one embodiment, a method of performing a fat grafting process on a patient includes: (1) harvesting an amount of fat from a donor site of the patient into a storage container; (2) treatment or preparation of the fat in various ways (for example centrifuging, filtering, gravitational separation, using the Revolve® system as shown in the views of FIGS. 9A, 9B and 9C)((3) positioning a delivery cannula into a first port of a grafting site of the patient; (4) pumping a portion of the amount of fat directly from the storage container into the first port of the grafting site of the patient until a first volume of fat is indicated on a pump used during the pumping step; and (5) positioning the delivery cannula into a second port of a grafting site of the patient; and (6) pumping a second portion of the amount of fat directly from the storage container into the second port of the grafting site of the patient until a second volume of fat is indicated on the pump used during the pumping step, wherein the pump used during the pumping step is in continuous communication with the storage container during the positioning a delivery cannula steps and the total of the first volume of fat and the second volume of fat is more than 120 cc.

These and other embodiments of the closed loop fat pumping method can include one or more of the following features. The step of pumping a portion of the fat can be performed at a rate of 10 ml/min to 350 ml/min. The grafting site of the patient can include a portion of the patient's face. The grafting site of the patient can include a portion of the patient's buttocks. The grafting site of the patient can include a portion of the patient's breast. The steps can be performed to accomplish a cosmetic effect at the grafting site. The steps can be performed to accomplish a reconstructive effect at the grafting site. The steps can be performed to accomplish a structural revision effect at the grafting site or any other part of the body with a soft tissue defect of either reconstructive or cosmetic nature, including by way of example, a scar deformity or other contour abnormality anywhere on the body. The steps can be performed to accomplish a bilateral breast construction at the grafting site. The steps can be performed as part of a cosmetic body contouring procedure.

In general, in one embodiment, a system for closed loop fat harvesting and continuous fat pumping includes an infiltration pump having operating characteristics for a tumescent infiltration delivery mode and a fat delivery mode, a length of infusion tubing adapted for use with the infiltration pump when operating the infiltration pump in the tumescent infiltration delivery mode, at least one infiltration cannula sized for use with the length of infusion tubing, a fat harvesting cannula and tubing to connect the fat harvesting cannula to a fat collection canister, and a length of infusion tubing adapted for use with at least one fat delivery cannula and with the infiltration pump when operating the infiltration pump in the fat delivery mode. The fat harvesting may be performed or assisted in its performance with power assisted liposuction (PALS®)

This and other embodiments can include one or more of the following features. The length of infusion tubing adapted for use with at least one fat delivery cannula can be from 4 to 6 feet. The length of infusion tubing adapted for use with at least one fat delivery cannula can have a volume of 150-200 cc. The fat delivery cannula can have a length between 10 to 15 cm and is between 12 to 16 gauge. The fat delivery cannula can be a 12 gauge microinjection cannula, a 14 gauge microinjection cannula or a 16 gauge microinjection cannula. The fat harvesting cannula can be a 2 mm size cannula, 3 mm size cannula, a 4 mm size cannula or a 5 mm size cannula. The infiltration pump operating characteristics in the fat delivery mode can be adapted to perform the methods.

BRIEF DESCRIPTION OF THE DRAWINGS

FIG. 5 is a flow chart of an exemplary embodiment of a closed loop high volume fat transfer method.

FIG. 21 is a table summarizing patient demographics of patients receiving treatment according to an embodiment of the closed circuit fat transfer method of FIG. 5.

FIG. 22 is a table summarizing outcomes of the patients discussed in FIG. X1.

FIGS. 14A, 14B and 14C (discussed above) are left oblique, frontal and right oblique views respectively of Patient 1's preoperative condition (i.e., upper row image panel). FIGS. 23A, 23B and 23C are left oblique, frontal and right oblique views respectively of Patient 1's condition observed at 8 months post-surgical follow up.

FIGS. 19A, 19B and 19C (discussed above) are left oblique, frontal and right oblique views respectively of Patient 4's preoperative condition (i.e., upper row image panel).

FIGS. 20A, 20B and 20C (discussed above) are left side, frontal and right side views respectively of Patient 5's preoperative condition (i.e., upper row image panel). FIGS. 25A, 25B and 25C are left side, frontal and right side views respectively of Patient 5's condition observed at 16 months post-surgical follow up.

DETAILED DESCRIPTION

Figure 1:
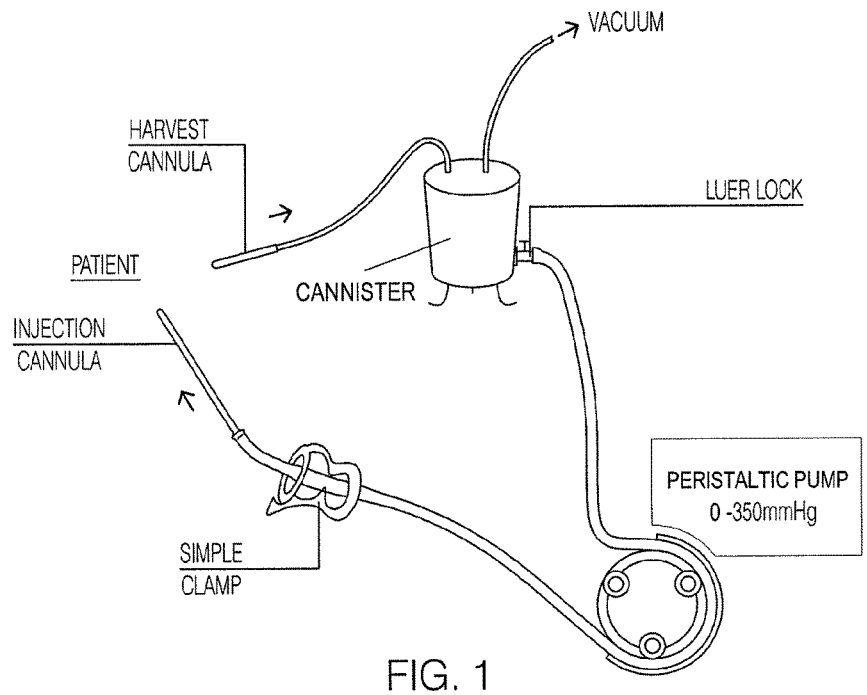
FIG. 1 is a schematic view of the arrangement of the separate components for the system and how they are connected together with respect to the flow and direction of the fat harvesting from the patient to the pump of delivery back to the patient.

In one aspect, there is provided method of harvesting and transferring large volumes of fat for grafting in a sterile closed circuit system. Embodiments of the inventive method provide a number of benefits, including:

a) Saves operating and anesthesia times
b) Limits spillage and waste of graft tissue
c) Decreases manual force needed
d) Decreases strain and fatigue on the surgeon's hands, and
e) Limits air exposure of graft material.
f) Maintains fat in sterile field throughout entire process.

Moreover, the system can be built using multiple interchangeable components already in use in various aspects of fat grafting and fluid transfer, but their cooperative utilization together as a system operated within particular parameters to increase viability of fat grafts provides a time and facility benefit greater than the sum of the parts alone.

In one specific aspect, the same size, gauge and type of tubing and infusion pump used during a tumescent infusion step is used to deliver harvested fat. More specifically, an infusion cannula and infusion tubing is coupled to an infusion pump and used for infiltration of fluids at the fat harvest site. The fat is harvested into a fat collection container. The fat may be processed according to a surgeon's individual preference, as in for example centrifuging, filtering, gravitational separation, using the Revolve® system. The Revolve® system may be used in the circuit as the collection canister. Thereafter, a new sterile 4 to 6 foot section of infusion tubing is connected in reverse orientation to the collection container, threaded through the same pump used during the infusion step. Thereafter, the infusion pump is operated to provide continuous, controllable, fat delivery to the fat grafting site via a suitable delivery cannula.

In various alternative aspects of this invention elaborates on the construction of a simple closed loop system for continuous flow harvesting, collection, syphoning, and grafting of large volumes of fat. As a result, this inventive system of methods uniquely bypass standard cumbersome and time-consuming process, mainly the need to first transfer fat into individual syringes prior to grafting into the patient. This method is traditionally done with unmeasured, manual pressures as generated by a simple plunger syringe. It can be messy and sloppy, with loss of fat. In contrast, this innovative methods and system presented here simplifies the whole process into a closed loop, from the patient donor harvest site, and then back to the patient. The concept is modular, drawing on commonly used, interchangeable parts and pumps present and available in most basic community hospital operating rooms. The major benefit is a significant reduction in time to transfer fat from patient donor or site to patient graft site. Additional advantages include a simplification of the process with less harvested fat air exposure time, consistent controlled limit on flow pressures, and a simple on off control that can be held in one hand, or controlled by foot pedal. Still further, the system is adaptable to standard liposuction and introduction cannulas through standard liposuction tubing and a luer lock connection. Moreover, the collection canisters are also interchangeable.

Figure 2:
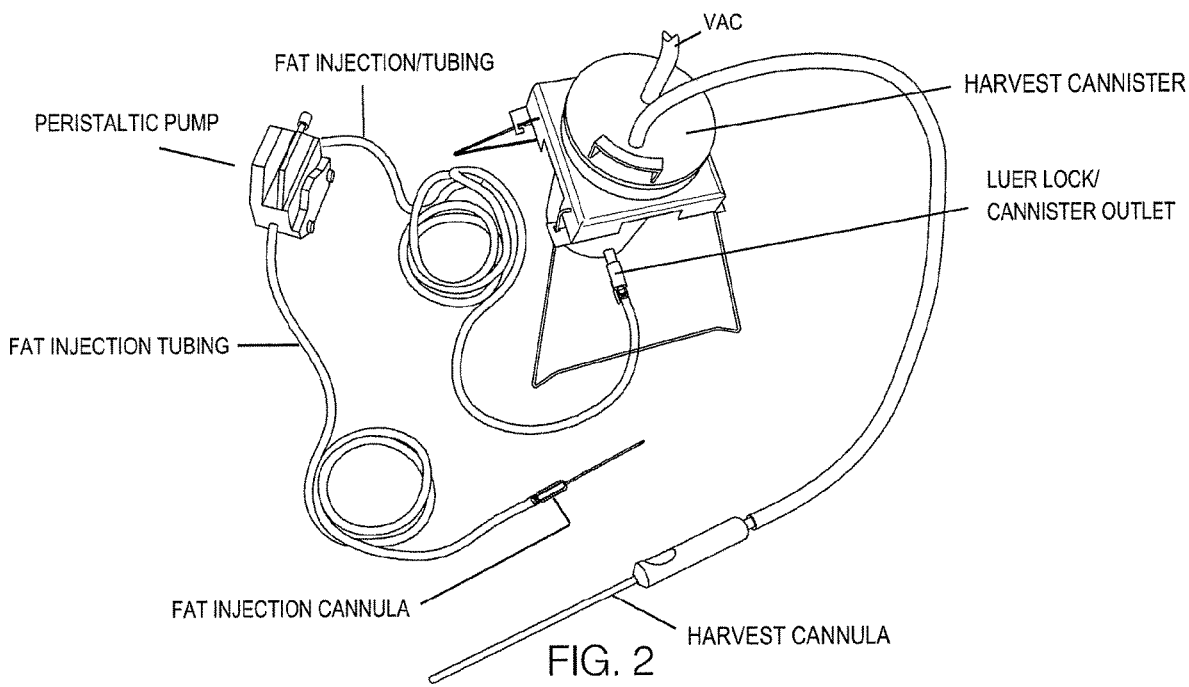
FIG. 2: Photograph of a prototype set up in the operating room, top down having a lipo-aspirate harvesting cannula (large at bottom) and fat introduction cannula (smaller adjacent to pump) directly attached to tubing. The collection canister is seen top center, and pump component is on the upper left.

A method of providing high volume fat grafting may be appreciated by reference to FIGS. 1, 2 and 5. FIG. 1 shows a schematic view of an exemplary closed circuit fat transfer system. FIG. 2 is a perspective view of an actual surgical set up used to practice an embodiment of the methods described herein. FIG. 2 shows how the harvesting cannula, collection canister, pump of delivery cannula are connected as one system—harvesting, processing and transfer with minimal air exposure and short time out side of the patient.

FIG. 5 is a flow chart of an exemplary closed circuit fat harvesting and transfer method 500. First, at step 505, there is a step of infusing a fat harvesting site of a patient with a tumescence fluid using a peristaltic pump. Next, at step 510, there is a step of harvesting an amount of fat from the fat harvesting site into a fat collection canister. Next, at step 520 there is a step of connecting a first end of a tube to an outlet of the fat collection canister and a second end of the tube to a fat delivery cannula. Next, at step 530, there is a step of engaging a portion of the fat delivery tube between the first end and the second end with the peristaltic pump. Next, at step 540, there is a step of operating the peristaltic pump to draw fat from the collection canister through the fate delivery tubing to the fat delivery cannula into a fat delivery site on the patient. In one alternative embodiment, harvesting step 510 is performed using a cannula coupled to a handle that induces movement such as variable and controllable vibration or oscillation in the cannula. In another or the same embodiment, such handle may be used with the cannula used for fat delivery as in step 540.

Turning to FIG. 1 and step 510, there is a step of Fat Harvesting: This may be done through a variety of techniques but basically any standard or preferred liposuction cannulas, connecting the liposuction tubing to a canister reservoir with an outflow luer lock, such as the JAC Cell®, Revolve® by PALS Microaire®, or other sterile collection system.

In one specific embodiment, a method of harvesting and grafting fat included a super wet tumescence step whereby 2-3 cc of tumescence fluid was injected into the patient harvesting site for every planned 1 cc harvested fat. This embodiment is a further specific example of the performance of steps 505 and 510 of the exemplary closed circuit fat transfer method 500.

The next step is processing.

This step may be done through the surgeons preferred technique, depending on the canister system used. If the JAC cell is used then the aqueous layer is allowed to decant and is first syphoned off through the luer lock connection. A warmer or heating element may be provided to maintain the harvested, separated fat at or near body temperature or to overcome cooling because of ambient conditions in the operating room. These and other variations are performed as part of harvesting step 510 which, like other steps of the exemplary method 500, are modified according to a number of practical factors, such as for example, the surgical skill and preferences of an individual surgeon performing the method as well as the clinical needs and circumstances of an individual patient receiving the benefits of the inventive method.

The next step is fat transfer.

Figure 3A:
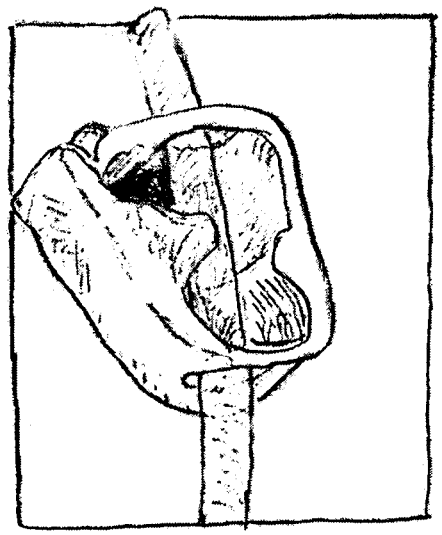
FIG. 3A: Perspective view of prototype of a control flow clamp for hand control of fat delivery rate.
Figure 6A:
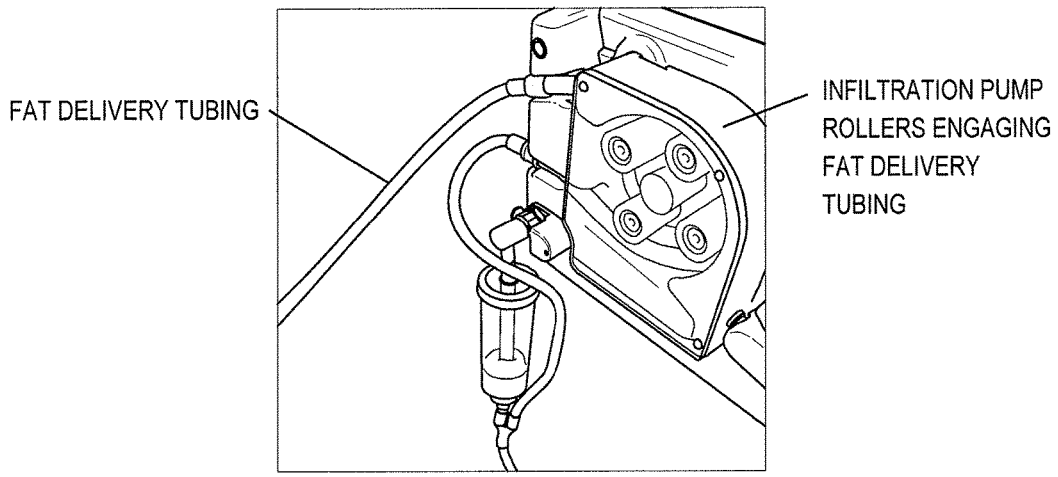
FIG. 6A is a perspective view of a fat transfer tube loaded into an infiltration pump and ready to perform a fat transfer step.
Figure 6B:
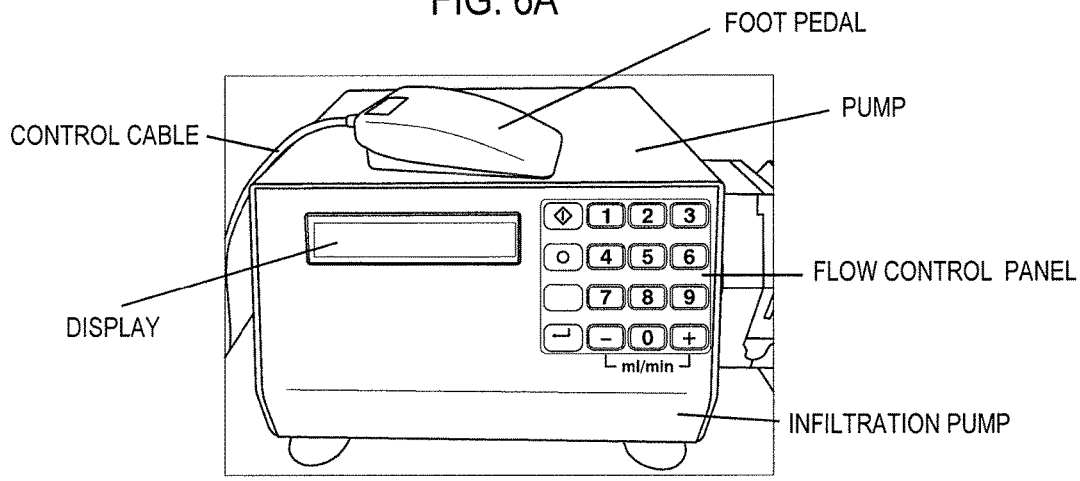
FIG. 6B is a front view of the control panel, display, foot pedal and cable for an infusion pump.
Figure 7A:
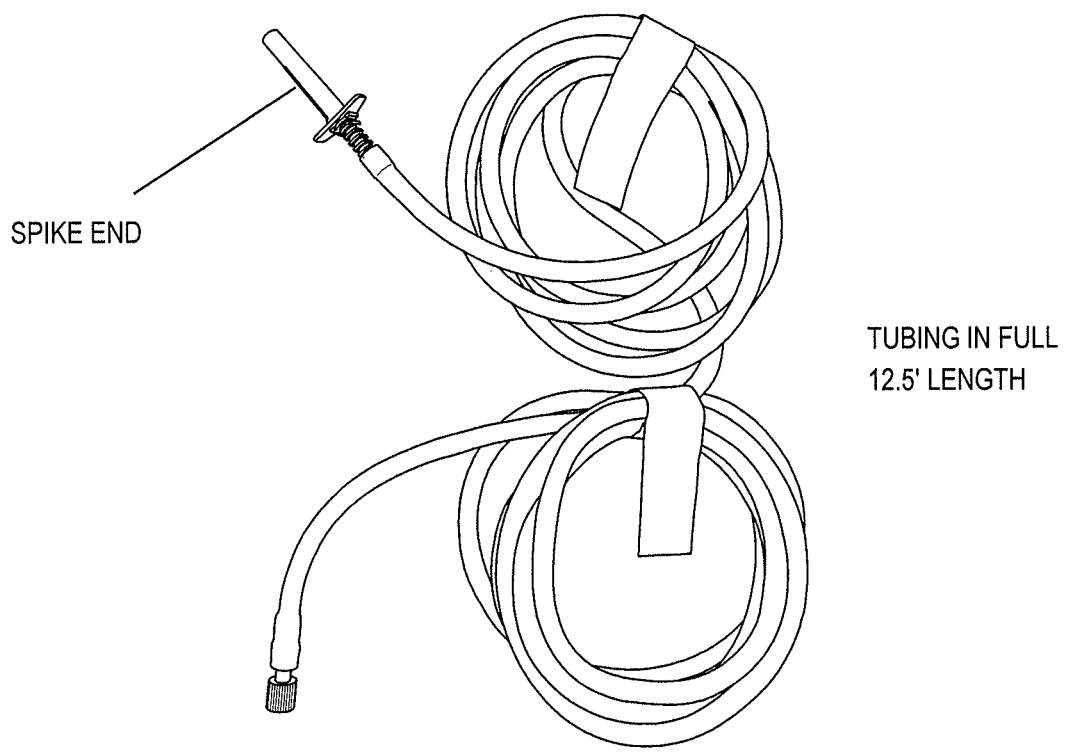
FIGS. 7A and 7B illustrate front views of infusion tubing within packaging (FIG. 7B) and prior to modification for use in the fat transfer method (FIG. 7A).
Figure 7B:
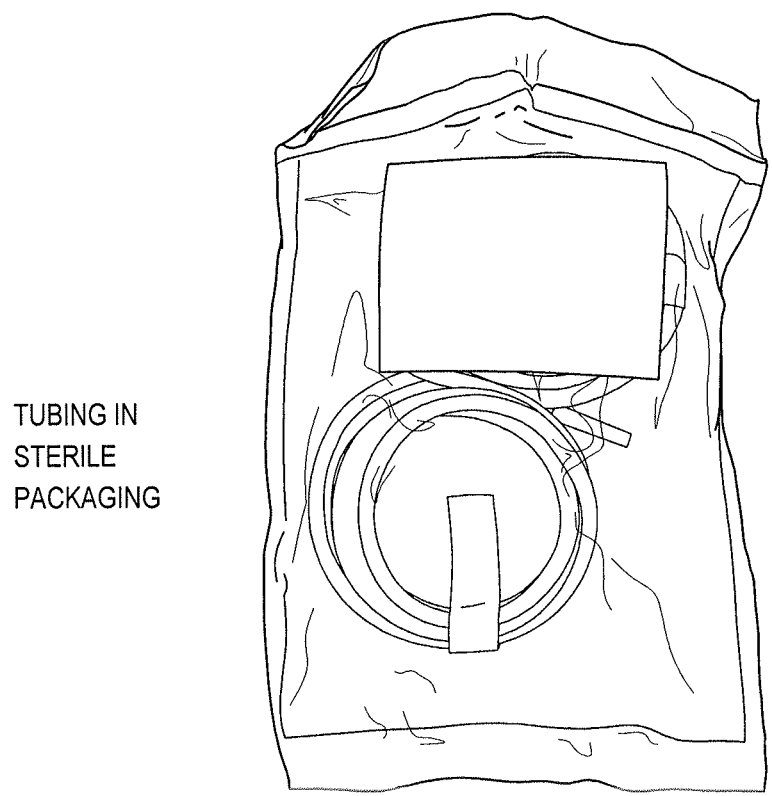
Figure 8:
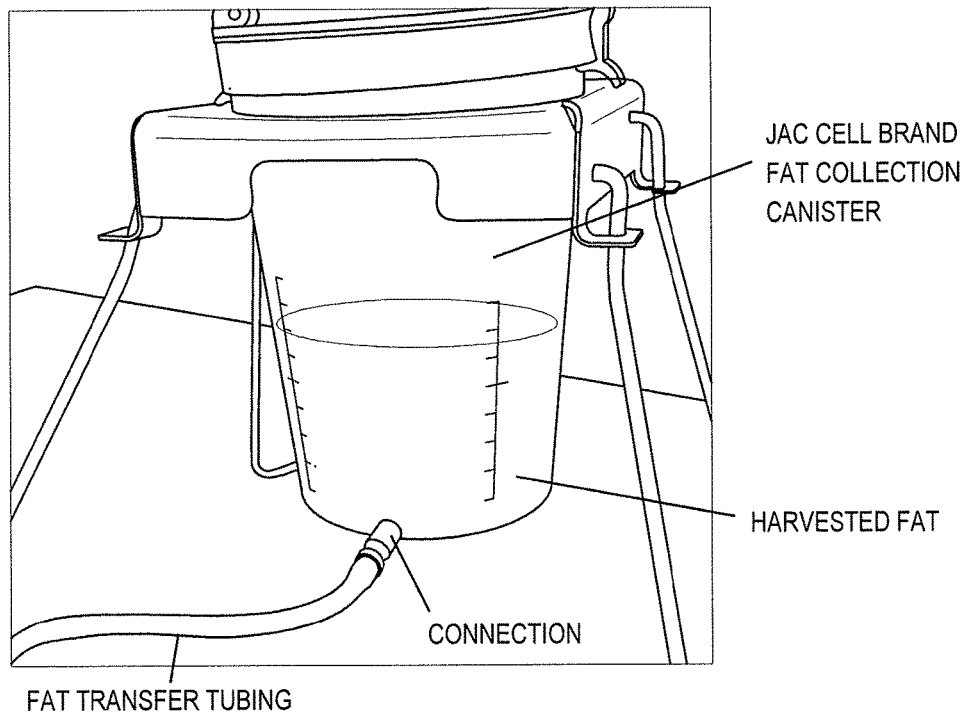
FIG. 8 is a perspective view of a fat connection canister after or during a fat harvesting step and shown connected to an end of fat transfer tubing.
Figure 9A:
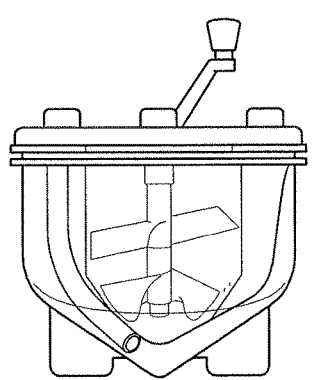
FIGS. 9A, 9B and 9C are side and top view of a mesh filter, internal propeller and top connections, respectively, of an alternative fat harvesting canister.
Figure 9B:
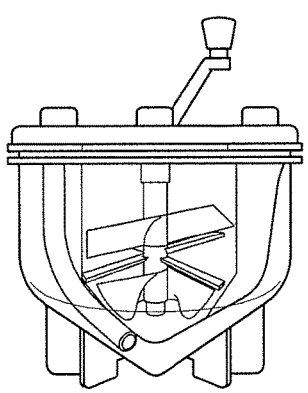
Figure 9C:
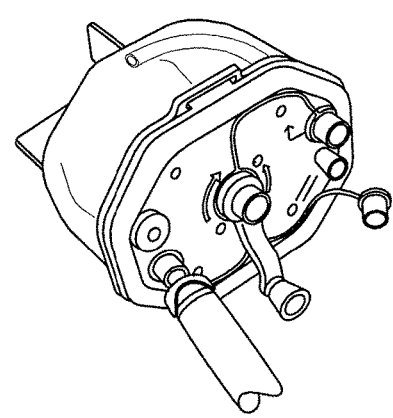
Figure 10A:
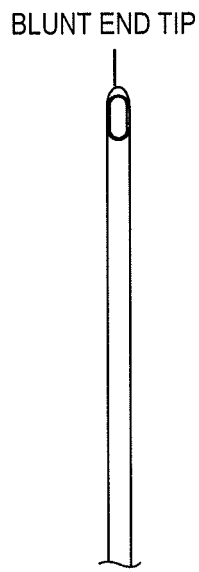
FIGS. 10A and 10B are top views of the distal ends of cannulas suited to the fat delivery method.
Figure 10B:
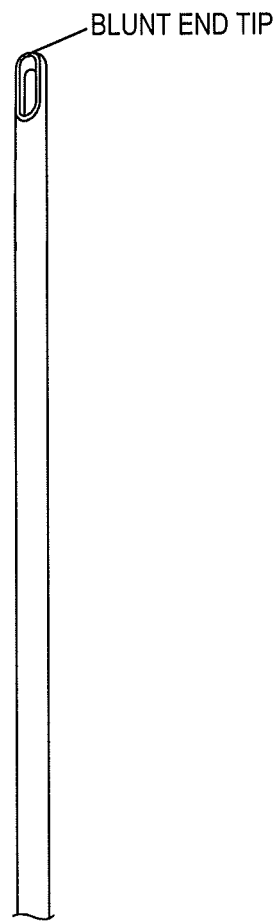
Figure 11A:
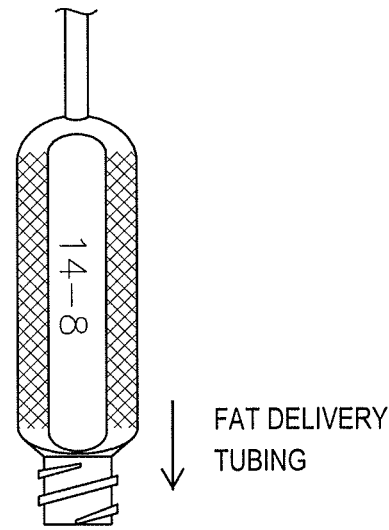
FIGS. 11A and 11B are top view of the proximal ends of cannulas suite to the fat delivery method.
Figure 11B:
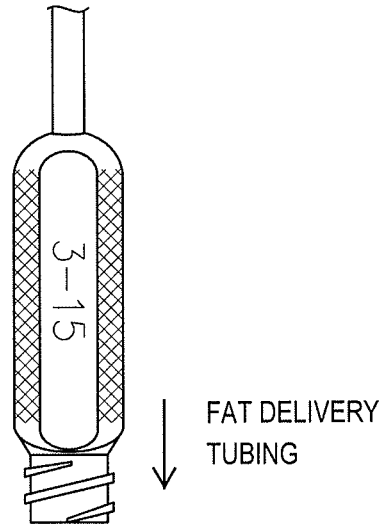
Figure 12A:
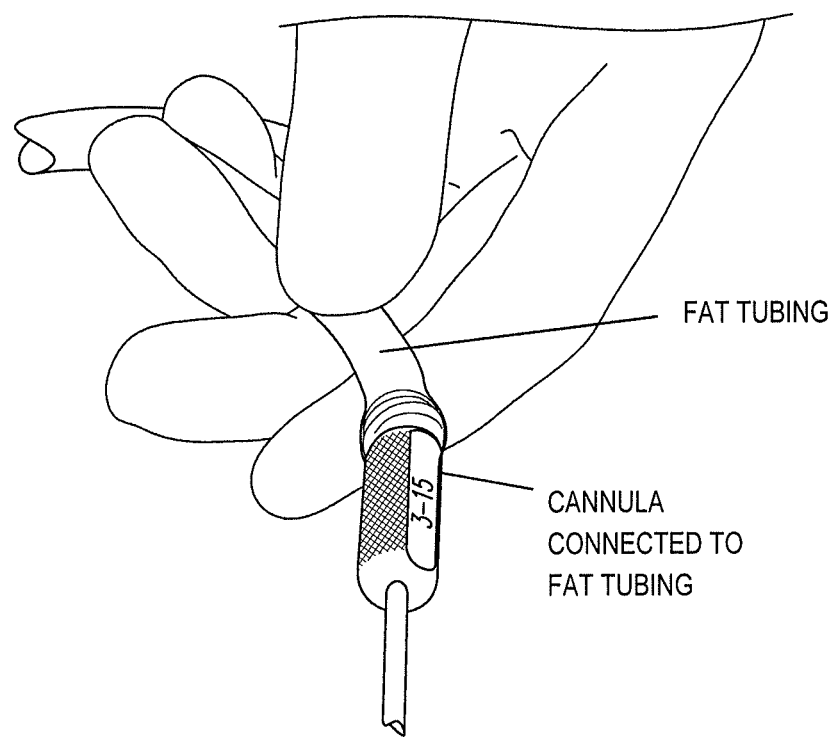
FIGS. 12A and 12B illustrate close up and prospective views of a fat delivery cannulas connected to a second end of fat transfer or infusion tubing.
Figure 12B:
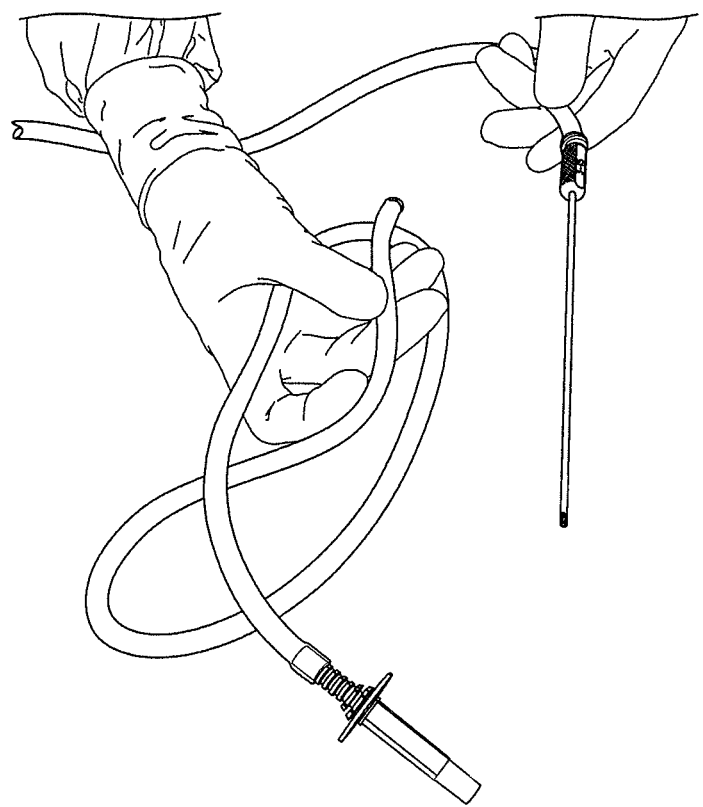
Figure 13:
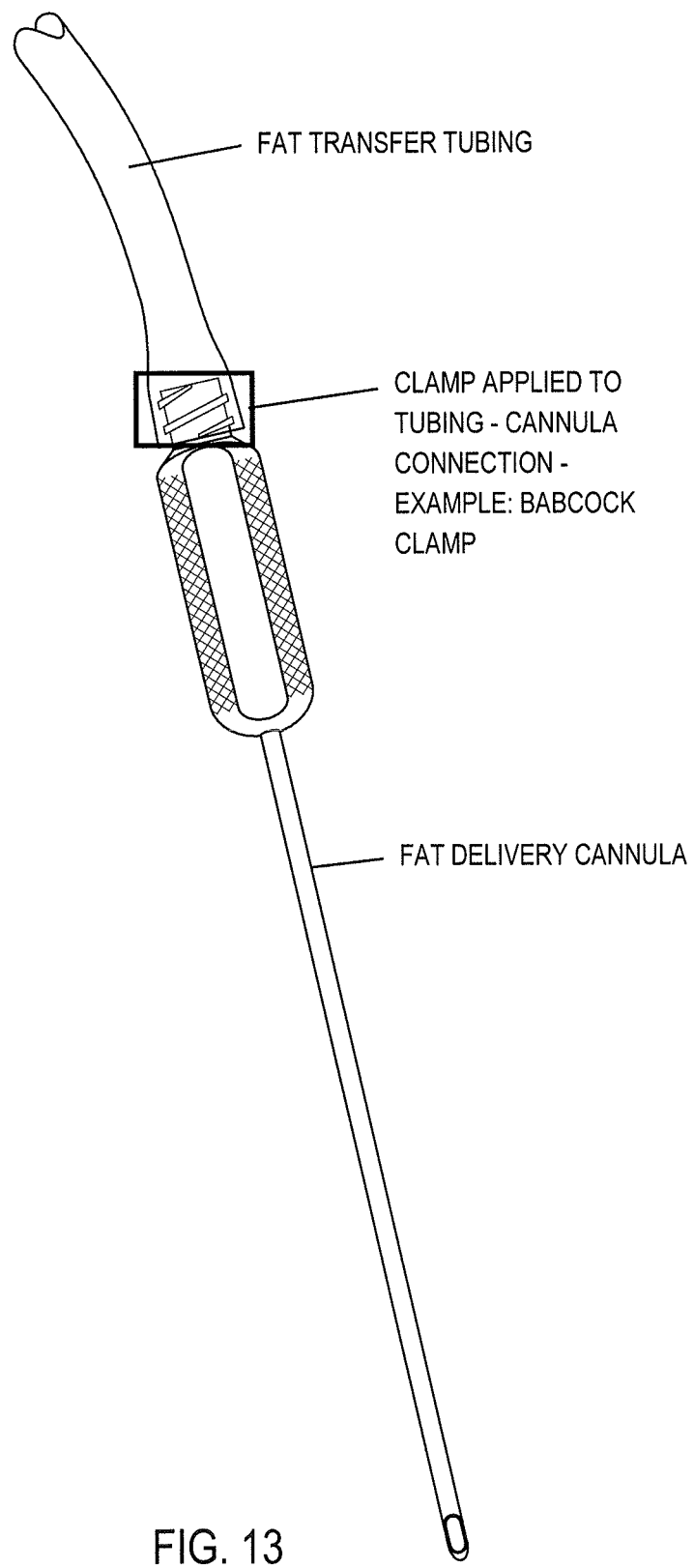
FIG. 13 is a perspective view of a fat delivery cannula connected to a second end of fat transfer infusion tubing having a clamp to reinforce the connection between the tubing and the cannula fitting.

In this step, a length of fat transfer tubing is appropriately threaded through a peristaltic pump before or after connecting a first end of the tubing to the outflow valve of the fat collection canister. (see steps 520 and 530) The tubing is shown in FIGS. 7A and 7B. For example the Arthrex® Pump with slightly wider bore tubing works well without clogging, but other tubing as well can be adapted (see, for example, FIGS. 3B, 4, 6A and 6B). Optionally, the Byron 'EZ pump'® tumescent infiltration pump may also be used. The two ends of the fat delivery tubing remain on the operative field with sterility preserved. The tubing can be directly connected to the harvesting canister and to most standard fat transfer cannulas. (See FIG. 5 steps 520, 530, and FIGS. 1, 4, 8, 12A, 12B and 13). Optionally, a flow control clamp (see FIG. 3) on the fat delivery tubing allows the operator manual flow control of the fat and introduction all with one hand, while the other hand is free to palpate tissue turgor, contour and position of the recipient bed or breast. Optionally, a babcock clamp or other simple clamp may be used to close the fat transfer tubing without damage.

In another embodiment, the foot pedal of the peristaltic pump is used to provide flow control of the fat thereby leaving both hands free to address fat introduction pattern, palpate tissue turgor, contour and position of the recipient bed or breast. FIG. 6B is a perspective view of an exemplary peristaltic pump, foot pedal and control cable.

Figure 3B:
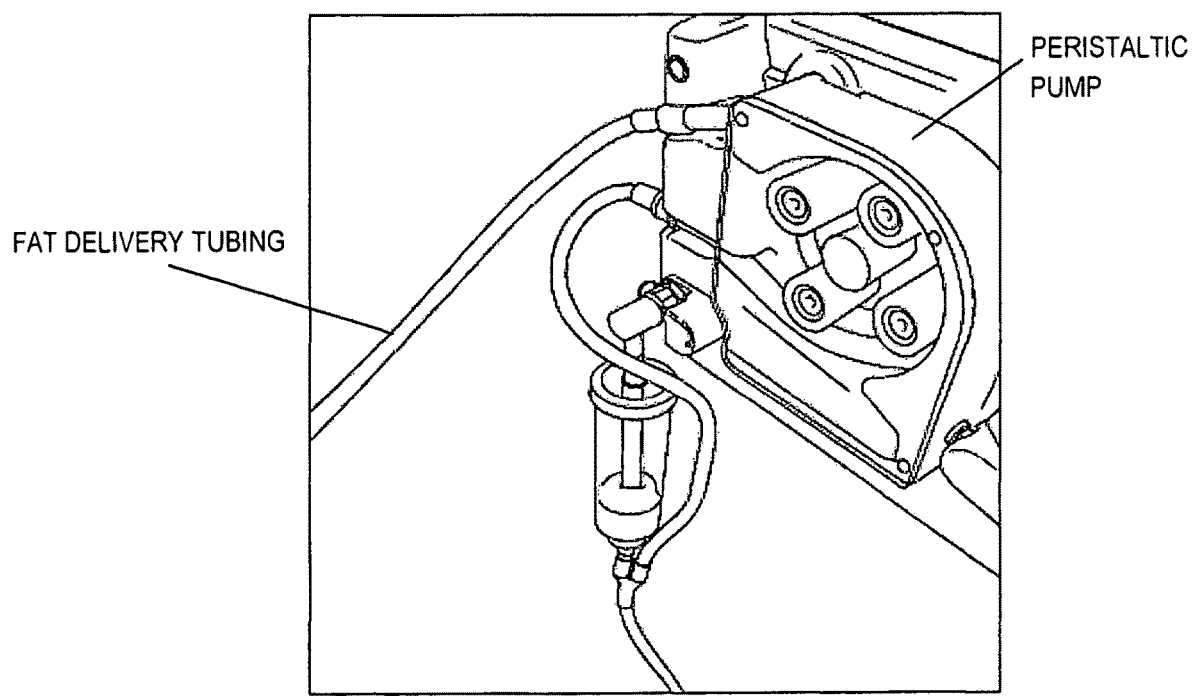
FIG. 3B: Perspective view of an alternative peristaltic pump to that of FIG. 2 that is loaded and charged with fat in tubing for transfer.
Figure 4:
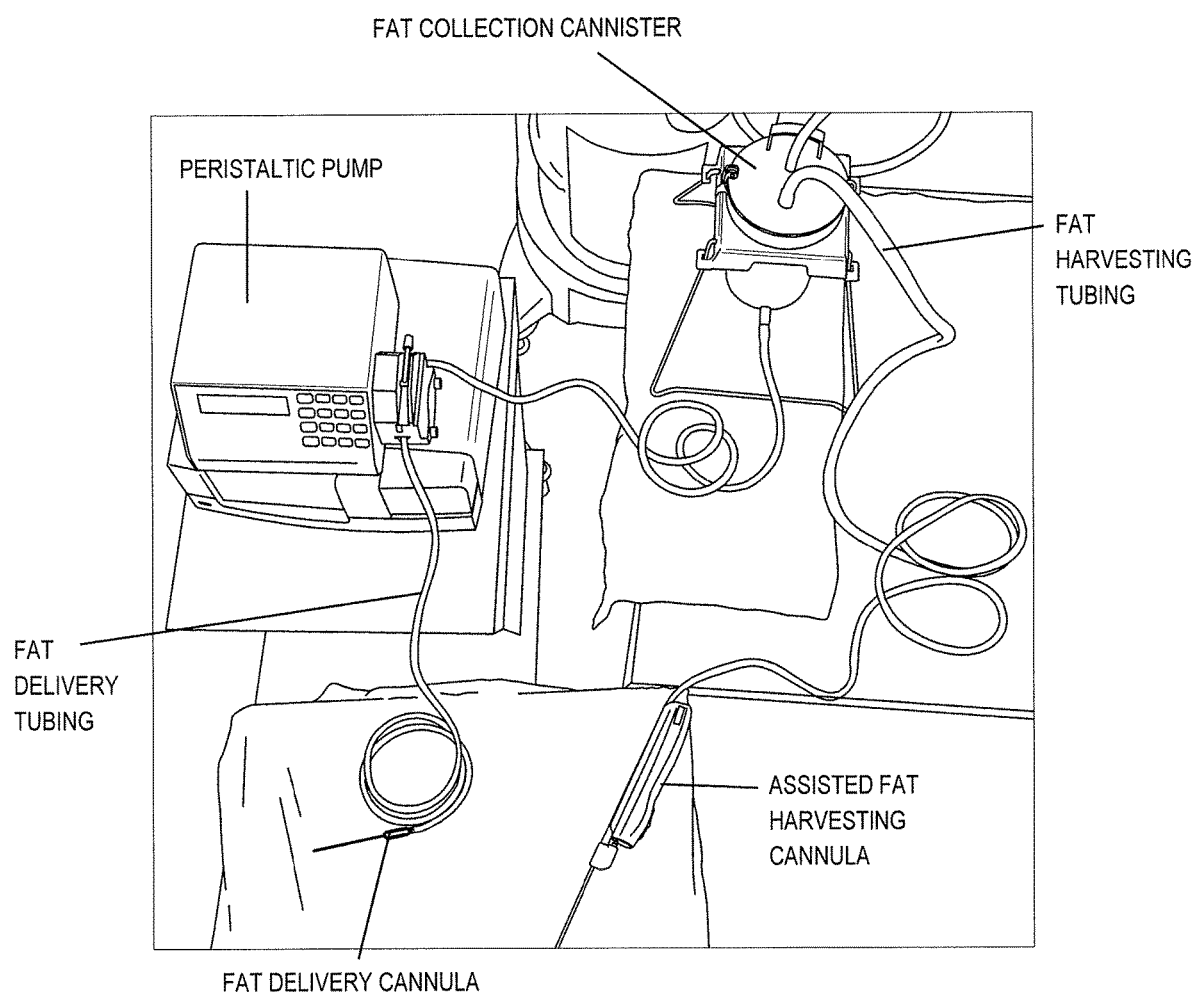
FIG. 4 is a perspective view, similar to FIG. 2, of a operating room set up for performing the closed loop fat transfer method.
Figure 6C:
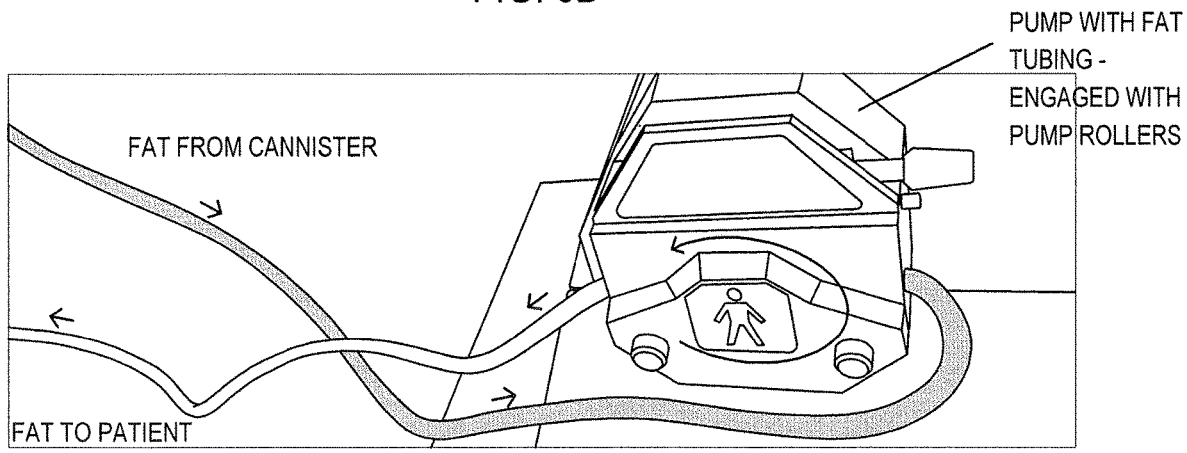
FIG. 6C is a perspective view of an infusion pump loaded with a length of fat transfer tubing for fat delivery.

Once the delivery tubing is loaded, the pump and tubing appear as shown in the exemplary set ups of FIGS. 2 and 4. FIGS. 3B, 6A and 6C are examples of fat loaded and flowing through pump. (See FIG. 5 step 540).

Exemplary cases, indications and techniques for fat grafting using embodiments of the closed loop pump system are provided below.

1) Reconstructive Breast:
a) Partial defects
b) Radiated tissue
c) Implant Volume Inadequacy in higher BMI patients
2) Cosmetic:
a) Large volume—eg. Buttock augmentation
b) Small volume—Facial Rejuvenation
Exemplary Technique:
Harvest:
Tumescent Fluid (ringers lactate with 1 amp bicarb and one 30 ml bottle on lidocaine with epinephrine 1:100,000 dilution) is infused with Byron EZ Pump® with expected ratio to harvested fat of 2-3:1. PALS Microaire® hand piece is used for assisted liposuction harvesting. Harvest cannulas of 3, 4 or 5 mm are used to harvest the fat. Suction is provided using a Neptune® system with pressures kept below 300 mmHg.

Collection:
Fat is collected in either JAC Cell® or Revolve® collection systems. A JAC Cell® system is shown connected to an end of fat delivery tubing in FIG. 8. With the former gravitation separates fat from supernatant, with some supernatant left in canister (5-10%) to ease fluidity of transfer. With the Revolve the fat may be washed with ringer's lactate solution in the standard fashion.

Grafting:
A second pack of infiltration tubing (i.e., Mentor CG tubing; see for example FIGS. 7A and 7B) that is used for the tumescent pump is then opened on the field in sterile fashion. The luer lock end is then attached to the collection system fat effluent gasket or port. The length of tubing is optimized to minimize pumping length (i.e., distance fat must travel within tubing) and provide enough maneuvering to reach the patient, which may vary with operating room set up dimensions, and user preferences. Tubing length from fat collection system outlet to grafting cannula is, for example, between 4-6 feet. The other tubing end is then fit onto the preferred injection cannula. Exemplary injection cannulas are 12, 14 or 16 gauge microcannulas. Various views of exemplary cannulas are provided in FIGS. 10A, 10B, 11A, 11B, 12A, 12B and 13. In some instances, a clamp may be attached over the tubing end to microcannula joint to prevent accidental blow off of the tubing from the cannula and possible loss of fat. In some aspects, the midpoint or a point spaced from about 1-2 feet from the collection canister, the tubing is then threaded in reverse fashion into the pump rollers. In some pump embodiments, a foot pedal is provided to control flow. Flow rates may be adjusted using pump controls or via foot pedal. In one aspect, fat delivery is initiated at 100 ml/min. The pumping rate may be adjusted depending on fluidity of fat which may change according to the bore of the harvest cannula, the amount of supernatant left with the fat, room temperature or other factors. In some aspects, one or more additive components may be incorporated into the harvest site or harvested fat in order to improve flow characteristics, graft viability, or other factors to improve closed loop fat transfer.

Sitting the patient upright, with all standard and proper protections is critical to assess contour changes prior to and during fat transfer. In these exemplary cases patients have both arms completely wrapped in foam and arm boards held out at 40 degree angles to the bed, and are also secured with a standard belt to the bed.

Illustrative Details for Individual Cases:

a) Reconstructive Breast—Partial Defects

For smaller volume partial defects or contour deformities: a finer cannula is used for harvesting fat, ranging in diameter of 3-4 mm. In some instances or for a portion of the harvesting a larger cannula up to 5 mm if the overall volume will be larger than 300 ml to 400 ml. In these cases the standard technique described above is used. If defects at the graft site are not due to specific scarring or issues of retraction as in radiation, then standard continuous pumping grafting introduction can be done while adjusting pumping speed or slowing or stopping the pump for grafting site assessment or manipulation. If the graft site defects are small, finer grafting cannulas sized between 14-16 gauge provide smoother transition contour. Additionally, flow rates can be commenced at lower rates such as 25 or 50 ml/min, and increased as needed, because smaller increments are needed to achieve a visibly noticeable change in small defect sites.

b) Radiated Tissue

First, the condition of the graft bed is assessed. Often radiated patients have more significant scarring, with adherence between the dermis and underlying structures that will impede grafting. Next, regions of adherence or scarring are released as needed to allow space for grafted fat. In one aspect, a V type dissector is advanced into the graft site and used to both make space and release skin for expansion to accommodate grafted fat. In these cases one does well to keep fat finer with harvest and with introduction, by the use of 3 mm for harvest and 12 gauge for introduction. In some embodiments, a patient receiving a continuous fat grafting procedure as described herein is followed using one or more auxiliary techniques such as external expansion both pre-op and post op to optimize graft success. Also fat is uniformly spread out through multiple trajectories, and if needed into muscle as well as subcutaneous planes (see R. Khouri and BRAVA pump or other similar devices).

c) Implant Volume Inadequacy/Higher BMI Patients

In the case of patient with higher BMIs whose native breast size and proportional goals may far exceed available implant volumes, fat grafting can be a much lower risk solution than autogenous tissue and more complex flap surgery with concomitant increase surgical risk and recovery times. For these larger volume grafts in otherwise healthy and not radiated tissue, larger cannulas may be used for harvest at 4 or 5 mm. Also larger introduction cannulas as well up as is in 10 to 12 gauge. More often seen in large patients with either overzealous or aggressive mastectomies are upper pole defects, or 'infraclavicular stepoff' as described by Kanchwala et al. with sharp transition contours between the 'breast versus subcutaneous adipose layers' due to the significantly larger layer of subcutaneous adipose tissue in the higher BMI patient. In these cases the pectoralis muscle can be utilized as a well vascularized bed for optimum grafting success and one or more steps of the continuous pumping grafting method is performed to graft fat into this region.

2) Cosmetic:

a) Large Volume—Buttock Augmentation

One additional benefit of the inventive methods is efficiency of transferring large volumes of fat cleanly, with the least amount of waste of both fat and time. Larger cannulas 5 mm for harvesting and introduction with large gauge microcannula selected in the range of 10-12 gauge. One or more steps of the grafting method are adapted to provide a supra-gluteal approach while avoiding deep muscular layers so as to prevent accidental intra-vascular fat injection.

b) Small Volume—Facial Rejuvenation

Much smaller volumes, in the range of 20-60 cc or in some embodiments in a range as small as 2-50 cc, harvest with smaller 2 mm cannula, inject with fat injection using 14-16 gauge blunt tipped microcannulas. With very low flow rates (10-25 ml/min), in these more finely detailed cases, the pump allows much more precision. Use of embodiments of the closed loop continuously pumping graft system provides consistent and controlled flow rates which prevent accidental over filling of the target graft site.

Results

In one exemplary surgical procedure using the harvesting, collection and pumping system described above, over 700 cc of harvested fat was delivered in 22 minutes as part of a graft to complete a bilateral breast reconstruction. The procedure was timed from the completion of harvesting fat from a patient, the connection of the delivery tubing to the collection canister and delivery cannula.

Exemplary procedures were performed with 5 patients using the techniques described herein including follow up in a range of 2 to 12 months with results described in Appendix A entitled "A Novel Closed Loop Fat Grafting System for Breast Reconstruction," and Appendix B titled "A Novel Closed Loop Fat Grafting System for Breast Reconstruction."

Patient 1

Figure 14A:
FIGS. 14A, 14B and 14C are left oblique, frontal and right oblique views respectively of Patient 1's preoperative condition.
Figure 14B:
Figure 14C:
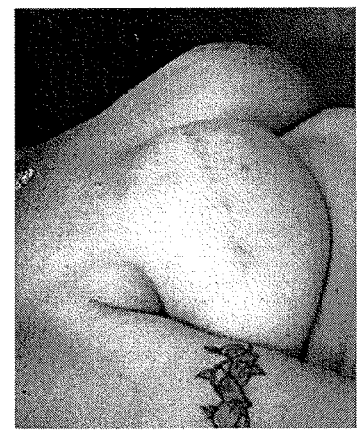
Figure 14D:
FIGS. 14D, 14E and 14F are left oblique, frontal and right oblique views respectively of Patient 1's condition observed at a----month post-surgical follow up.
Figure 14E:
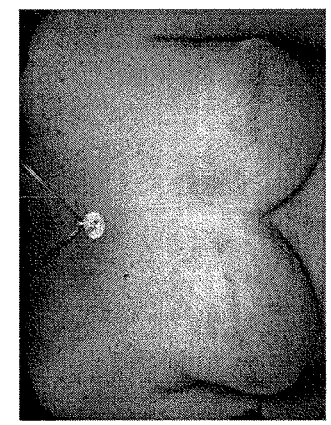
Figure 14F:
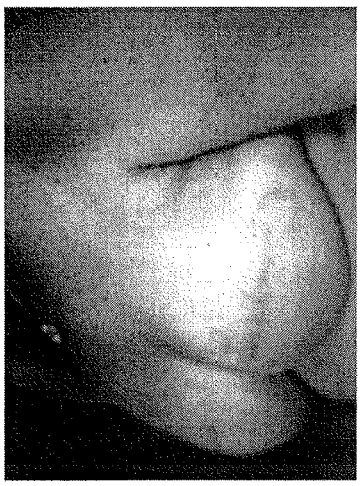

58 year old female post bilateral mastectomy for left breast DCIS with severe upper pole hollowing from overly aggressive mastectomy, as well as rippling on leaning forward due to thin mastectomy flaps. FIGS. 14A, 14B and 14C (upper row) show pre-op right oblique, frontal and left oblique views with markings for planned fat grafting and contour defects as described above. She had no radiation, BMI 28, and a total of 435 left, 360 cc fat to left breast over 20 minutes. Harvest fat was done from the abdomen with a 4 mm trochar and PALS Microaire® system, infusion was done through combination of 12 and 14 gauge Colemann® microcannulas with a single distal side opening, with an average rate of 150 ml/min, using the Byron EZ® pump. The lower row of pictures in FIGS. 14D, 14E and 14F are similar views of Patient 1 at 2.5 months post grafting with good improvement of upper pole hollowing, natural tear drop shape of breast and smooth slope of upper pole in lateral views compared to irregular divots seen in the upper preop views.

Patient 2

68 year old female with more complex history. She was referred from another institution, with a long history of metachronous (two separate) breast cancers. The right had been radiated and reconstructed with a large TRAM flap, the left with a latissimus dorsi flap and an implant. The implant had failed and was removed. She then underwent radiation to complete the cancer treatment over the LD flap. She was left with a huge discrepancy in volume, and no available pedicle flaps for transfer. Furthermore she did not wish any more flap surgery or any more implants. Therefore she underwent a combination of serial fat grafting along with pre and postoperative external expansion, along the method of Khouri, with both a BRAVA® device and later a Noogleberry® device. Furthermore, a wound VAC® (KCI) was used to power the pump aspect of the device because standard pump apparatus was inadequate.

Initially we tried to expand the left side before fat grafting but her chest wall skin was too thin and tight and a good seal could not be maintained with the BRAVA device. Therefore the first grafting was not just to the breast but also to the chest wall. To improve the quality of the radiated tissue.

Figure 15A:
FIGS. 15A and 15B are pre-operative frontal and left oblique views, respectively, of Patient 2.
Figure 15B:
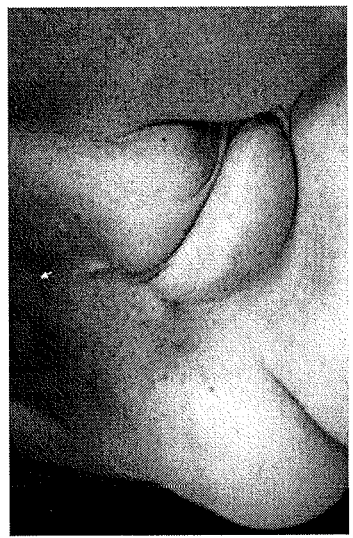
Figure 15C:
FIGS. 15C and 15D are 3 weeks post-operative follow up frontal and left oblique views, respectively, of Patient 2.
Figure 15D:
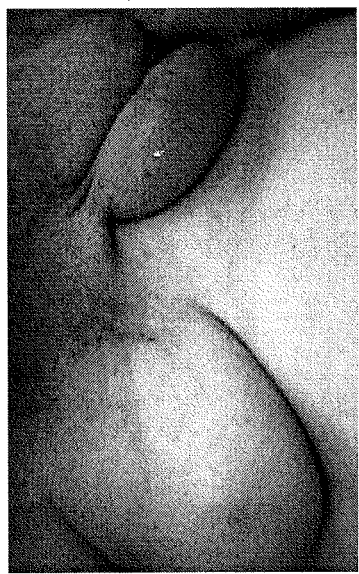

The upper row pictures in FIGS. 15A and 15B show preoperative frontal and left oblique preop views and the lower row (FIGS. 15C, 15D) showing the same views 3 weeks after 400 cc fat to left breast and chest wall. Note on the lower views of FIGS. 15C and 15D show the chest wall is filled out to a flatter wider base. The upper views in FIGS. 15A and 15B had firmer thinner, fibrotic tissue which is hard to appreciate visually, but this improved tissue quality allowed for better application of the external suction device over the breast mound. It can also be appreciated after just one fat grafting session that the lower pole and upper pole have greater volume, with the lower pole now showing a more pendulous lower breast.

Figure 16C:
FIGS. 16A, 16B and 16C are views of the right breast of Patient 2 after first cycle fat grafting, during external suction expansion process and after external suction and expansion process.
Figure 16B:
Figure 16A:
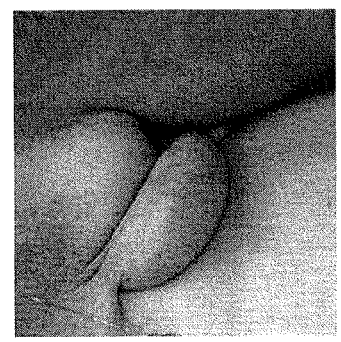
Figure 17C:
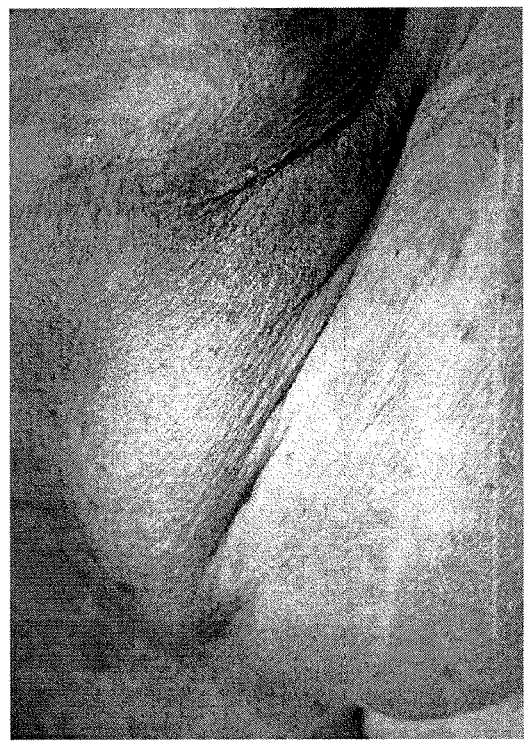
FIG. 17C is a close up view of a portion of the left breast of Patient 2 after performing external vacuum expansion.
Figure 17A:
FIG. 17A is pre-operative oblique view of Patient 2.
Figure 17B:
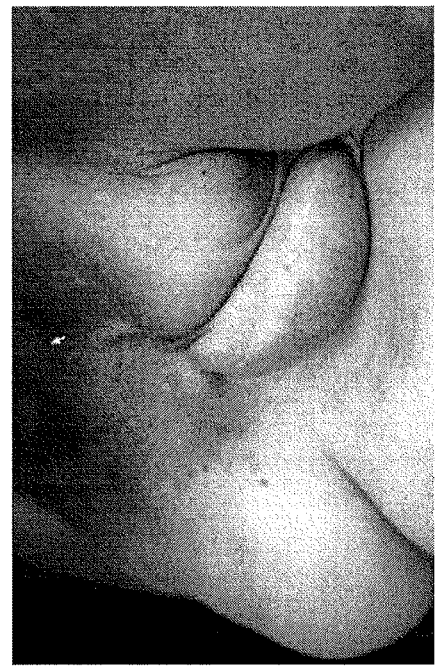
FIG. 17B is a left oblique view of Patient 2 after grafting 400 cc fat.

In the lower set of views for the same patient, the left side picture (FIG. 16A) shows a frontal view after fat grafting, but before expansion. The central larger picture of FIG. 16B shows the amount of expansion from the device over top of the grafted fat in a left oblique view. Note in the pre-op upper views in FIGS. 15A and 15B there is a severe scar constriction horizontally over the breast. During the first surgery, prior to grafting a V dissector was used to aggressively release as much of this scar and tethering to allow expansion of the envelope and accommodation of the fat graft. In the lowermost pictures (see FIGS. 16C, 17C) close up, you can see how now the skin is now free to expand out almost to the point that the stricture is not visible. You can see also how the expansion persists after removal of the device.

Intra-operatively she had fat harvested abdominally, using similar super wet tumescence protocol, a 4 mm harvesting cannula, AJC cell collection and re infiltration at 125 ml/min with a 12 gauge cannula and a Byron EZ pump.

Patient 3

Figure 18A:
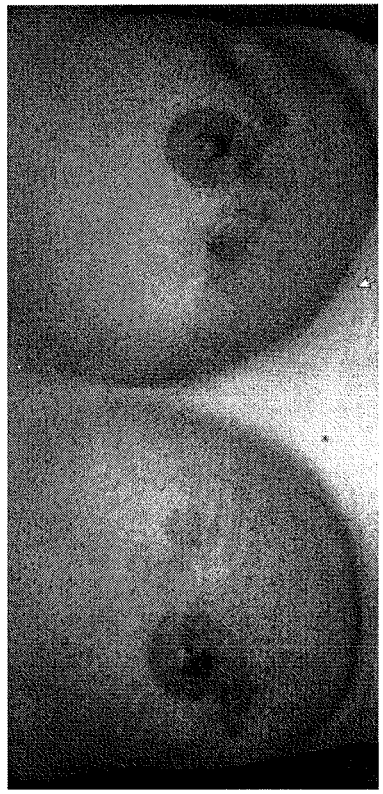
FIG. 18A is a frontal view of Patient 3's preoperative condition.
Figure 18B:
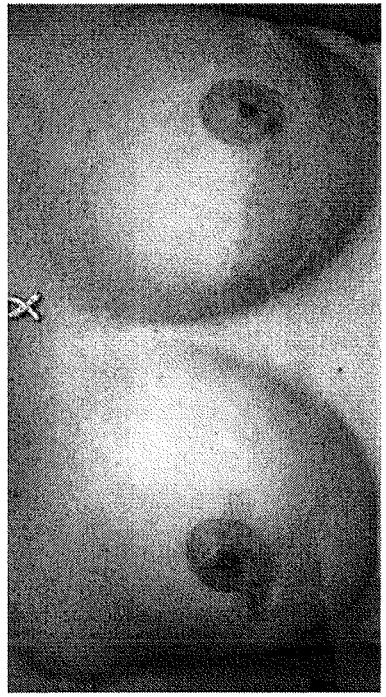
FIG. 18B is a frontal view of Patient 3's condition observed at a 1 month post-surgical follow up.

49 year old female with lobular breast cancer T1c who had bilateral mastectomy and TE/implant based reconstruction. She has some thin flaps in the lower pole, and needed a revision to her NAC (nipple areola complex). She had only 200 cc fat total, 75 cc to her right breast and 125 to the left, mainly in the lower pole. This was done with a 4 mm harvesting cannula, Byron pump and 12 and 14 gauge injection micro-cannulas, over 15 minutes at an average of 100 ml/min. The main grafting was done to the bilateral lower poles. FIG. 18A is the pre-op frontal view on the left. FIG. 18B, as can be seen in the right picture, is the postoperative shot at one month, a subtle improved fullness, or rounding out of the lower poles on both sides. With the best results seen in her right breast lower pole. Her left breast still has some scar tissue laterally which prevented better graft expansion. She may benefit from an external expansion device over that aspect to pull out the skin, and more fat after that.

Patient 4

Figure 19A:
FIGS. 19A, 19B and 19C are left oblique, frontal and right oblique views respectively of Patient 4's preoperative condition.
Figure 19B:
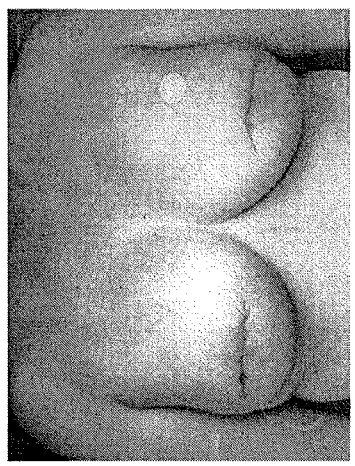
Figure 19C:
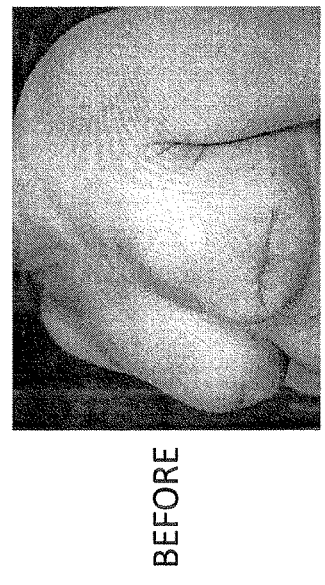
Figure 19D:
FIGS. 19D, 19E and 19F are left oblique, frontal and right oblique views respectively of Patient 4's condition observed at a 11.5 month post-surgical follow up.
Figure 19E:
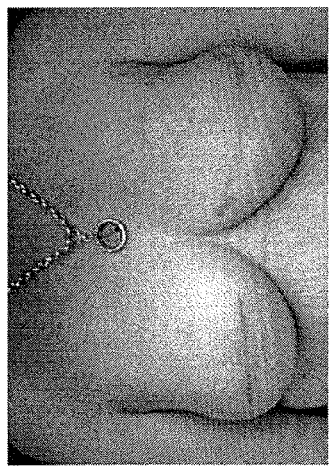
Figure 19F:
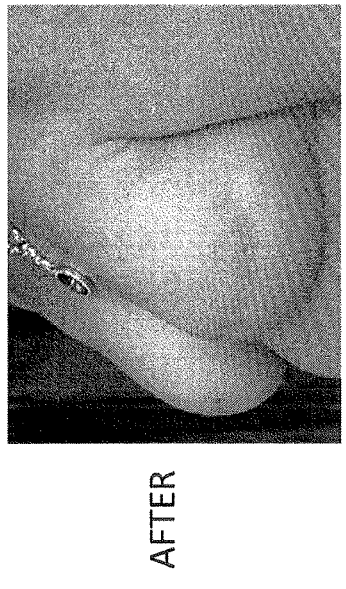

39 yo female with DCIS left who underwent biopsies and ultimately bilateral mastectomies and reconstruction. Her left breast envelope was asymmetrical to the right. FIGS. 19A, 19B and 19C are the upper views pre grafting and show a flat, tight slope on the left breast, especially medially (seen in the left lateral oblique view of FIG. 19A), as well as a drooping lower pole on that side. The lower views of FIGS. 19D, 19E and 19F are post grafting and almost 1 year. She also had revision of the left breast skin envelope, revising the skin in the lower pole to improve the shape. In the views of FIGS. 19D, 19E and 19F, you can see a more natural breast appearance with improved volume overall, more projection and fullness to the lower pole especially on the left breast in the lateral views, and a more pleasing and natural overall appearance. She has had some gravitational descent of the implants on both sides, but because of the fat grafting to the upper poles, she has not developed any hollowing or rippling, and maintains a natural upper pole slope. Her procedure had 325 cc to the left breast and 25 to the right, a 4 mm harvesting cannula, and an Arthrex pump was used with 12 and 14 gauge cannulas over 20 minutes, with infusion rates up to 200 ml/min.

Patient 5

44 year old female with left breast cancer with nodal mets. She had bilateral immediate reconstruction with TE and then had radiation over the left breast with the TE in place. 3 months later she had bilateral implant exchange and fat grafting. The pictures in FIGS. 20A, 20B and 20C (the upper row) show her post TE and left sided radiation, prior to grafting and implant exchange. FIGS. 20D, 20E and 20F (the lower row) show her 1 year post implant exchange and fat grafting. It is clear that she has still got great improvement in lower pole contour roundness and overall softening of the shape. The left breast still has some irregular due to irradiation, with a slight wide V shape to the lower pole, but the patient is very happy with her reconstructed breasts. You can see also in the upper row pre-op photos of FIGS. 20A, 20B and 20C, an obvious shadow and scar on her right breast upper medial pole where she had a port-o-cath placement for chemotherapy that had been recently removed. In FIGS. 20D, 20E and 20F, even one year out, she has persistence of the improved contour under the port scar which was obtained through grafting fat in that area at the time of exchange.

Further, in a recent review by Sinno et al[7], notes that during fat harvesting procedures there is now 'good evidence that pumping fat versus syringe action has no difference in fat survival'. While desiring not to be bound by theory, the methods of high volume fat transfer described herein are believed to produce similar positive results for survival of pumped fat techniques for introducing the fat back into the graft site. Moreover, the closed loop system and methods described herein also enable the unmet need articulated in literature namely that 'fat should be injected soon after harvesting, as properties of fat begin to change after processing'. As a result, embodiments of the present high volume closed loop continuous fat pumping system provide the two-fold utility of more rapid fat delivery without harming the grafted fat and decreasing the transfer time delay between donor site harvesting to graft site delivery.

Given success of first five patients we obtained an IRB to analyze outcomes with a group of successive patients, with a single surgeon, consistent harvesting technique, and consent for use of a modification of a surgical technique. Explanation was given to patient regarding the nature of the modification, mechanizing an otherwise manual technique, in order to shorten operating time. Patients were given option to decline novel variation of technique, but otherwise it was applied to all patients presenting for grafting. No patient declined. Component times for infiltration of tumescent, harvesting and fat grafting were recorded, as well as volumes and pump rates. Patients were followed in usual manner for clinical outcomes, and complications, with photos taken as per standard protocol. Patients were also followed up by their oncologist and general surgeon.

For the remainder of the patients we used more of the Byron EZ pump, and varied use of the harvest cannulas down to smaller diameters for better fat quality. This was experimented with because sometimes the fat would get stuck or block in the smaller 14 or 16 gauge microcannulas, when a 4 mm harvest cannula was used. Thus we experimented with 2, 3 and 4 mm harvest cannulas and 12 and 14 and 16 gauge microcannulas.

Patient Demographics are provided in FIG. 21 and summarized as follows:

Average age 53(36-69) BMI 28.5 kg/m$^2$ (28-39). There were no smokers. 6 of 15 patients had radiation prior to grafting, and 7 of 27 breasts. 1 patient was diabetic and 5 were hypertensive.

Outcomes are provided in FIG. 22. The outcomes may be summarized as follows:

Total mean volume of fat grafted was 407 cc range (200-795) with mean 271 (125-435 cc) to the left breast and 125(0-360) cc to the right breast. There was a disproportionately great number of patients with breast cancer on the left side. 9 patients had left sided disease, two had bilateral, one prophylactic for BRCA 1 carrier status and only 3 had right sided disease. Average time to transfer fat was 18.5 minutes (range 15-25), with an average infusion rate of 146 cc/min range (100-250 ml/min). Mean follow up was 6 months, range 1-18 months. Two patients had minor complication of red breast treated with oral antibiotics only with resolution. One of these patients later developed a pinhole opening over the exchange scar and underwent washout and exchange for a new sterile implant with good outcome. One patient developed 2 subcutaneous small granulomas (subcentimeter) confirmed on ultrasound.

Additional evidence of clinical and aesthetic long term outcomes has been demonstrated in 3 separate patients at 8, 12, and 16 months follow up. These three patients are part of the original five patients discussed above.

FIGS. 14A, 14B and 14C (discussed above) are left oblique, frontal and right oblique views respectively of Patient 1's preoperative condition (i.e., upper row image panel). FIGS. 23A, 23B and 23C are left oblique, frontal and right oblique views respectively of Patient 1's condition observed at 8 months post-surgical follow up.

Figure 24C:
FIGS. 24A, 24B and 24C are left oblique, frontal and right oblique views respectively of Patient 4's condition observed at 12 months post-surgical follow up.
Figure 27B:
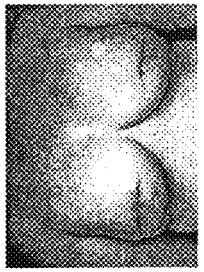
Figure 24B:
Figure 27A:
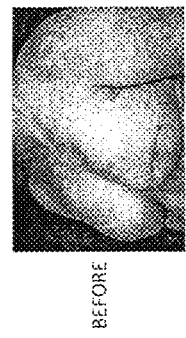
Figure 24A:
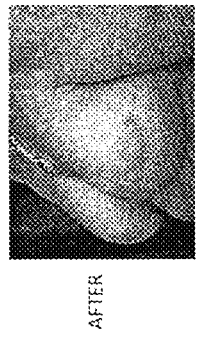

FIGS. 19A, 19BV and 19C (discussed above) are left oblique, frontal and right oblique views respectively of Patient 4's preoperative condition (i.e., upper row image panel). FIGS. 24A, 24B and 24C are left oblique, frontal and right oblique views respectively of Patient 4's condition observed at 12 months post-surgical follow up.

Figure 20C:
FIGS. 20A, 20B and 20C are left side, frontal and right side views respectively of Patient 5's preoperative condition.
Figure 20B:
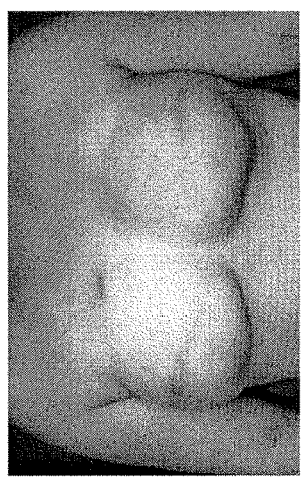
Figure 20A:
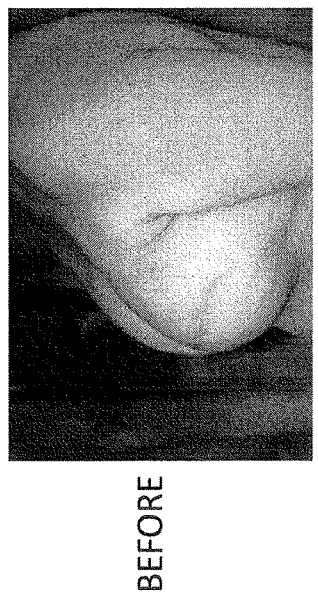
Figure 20F:
FIGS. 20D, 20E and 20F are left side, frontal and right side views respectively of Patient 5's condition observed at a 12 month post-surgical follow up.
Figure 20E:
Figure 20D:
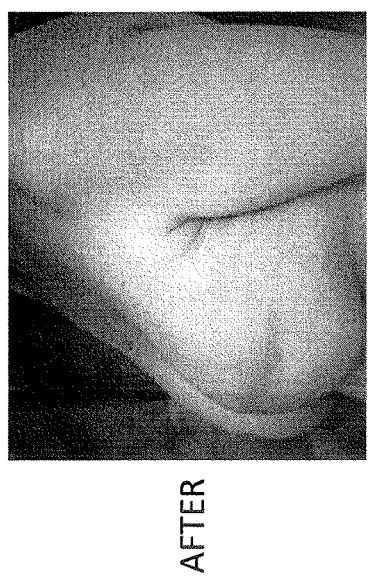
Figure 27C:

FIGS. 20A, 20B and 20C (discussed above) are left side, frontal and right side views respectively of Patient 5's preoperative condition (i.e., upper row image panel). FIGS. 25A, 25B and 25C are left side, frontal and right side views respectively of Patient 5's condition observed at 16 months post-surgical follow up.

As seen in the comparison of the pre-operative and follow up images discussed above, all three patients show significant persistence of grafted fat in lower row follow up photos with significant maintained improvement over preoperative photos (upper row in each patient view).

Additional details are provided in U.S. Patent Application Publication No. US2015/0209565, U.S. Patent Application Publication No. US2005/0084961, U.S. Pat. No. 8,632,498, U.S. Patent Application Publication No. US2009/0287190, U.S. Patent Publication No. 2013/0324966 and U.S. Patent Application Publication No. 2012/0253317, as well as in these references:

1. Spear S L, Wilson H B, Lockwood M D. Fat injection to correct contour deformities in the reconstructed breast. Plast Reconstr Surg. 2005; 116:1300-1305.
2. Coleman S R, Saboeiro A P. Fat grafting to the breast revisited: Safety and efficacy. Plast Reconstr Surg. 2007; 119:775-785;
3. Delay E, Garson S, Tousson G, Sinna R. Fat injection to the breast: Technique, results, and indications based on 880 procedures over 10 years. Aesthet Surg J. 2009; 29:360-376.
4. Khouri R K, Rigotti G, Cardoso E, Khouri R K Jr, Biggs T M. Megavolume autologous fat transfer: Part I: Theory and Principles. Plast Reconstr Surg. 2014; 133:550-557.
5. Khouri, Roger K. M. D.; Rigotti, Gino M. D.; Cardoso, Eufemiano M. D.; Khouri, Roger K. Jr. B. S.; Biggs, Thomas M. M. D. Megavolume Autologous Fat Transfer: Part II. Practice and Techniques. Plast Reconstr Surg. 2014; 133:1369-1377.
6. Khouri, Roger K., Jr., BS, Khouri, Raoul-Emil R., Lujan-Hernandez, Jorge R., et al, "Diffusion and Perfusion: The Keys to Fat Grafting," Plast Reconstr Surg Glob Open. 2014 September; 2(9): e220, published online 2014 Oct. 7.
7. Sinno S, Wilson S, Brownstone N, Levine S M. Current Thoughts on Fat Grafting: Using the Evidence to Determine Fact or Fiction. PRS 2016 March; 137(3):818-24.
8. Kanchwala S K, Glatt B S, Conant E F, Bucky L P. Autologous fat grafting to the reconstructed breast: The management of acquired contour deformities. Plast Reconstr Surg. 2009; 124:409-418.

As will be appreciated by considering the details of the various embodiments described herein, the inventive closed loop, continuous pumping fat grafting system provides a number of advantages over conventional syringe based or small volume transfer systems. Conventional manual systems require additional handling steps to load syringes or other equipment while the inventive system pumps directly from the harvested fat storage container to the grafting site using a single tube. The inventive pumping system provides for single hand operation without tiresome mechanical actuation required by syringe delivery. Advantageously, the inventive closed loop continuous pumping system provides real time response via foot pedal or flow control valve or clip in order to increase, decrease, pause or resume pumping action in response to real time user assessment including visual observations, measurements, tactile responses or manipulations of the grafting site, depending upon procedure. Advantageously, the inventive system reduces the need for equipment by employing the same size tubing and infusion pump for the initial tumescent infiltration step as for the later fat deliver step. In one aspect, the operating parameters of the pump have preset limits or ranges of operation for use during infusion and another set of preset limits or ranges of operation for use during fat delivery. It is to be appreciated that selection of roller and tubing materials, adjustments to roller speed, tubing properties and roller-tubing hardness may be optimized to minimize or reduce shear or other forces imparted to pumped fat while still providing sufficient or desired tumescent infusion properties or pumping characteristics. As a result, aspects of the inventive closed loop fat transfer system may use the same pump with different operating characteristics for both the infusion step as well as for the fat delivery step thereby further increasing the efficiency of fat harvesting and transfer operations.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of performing a fat grafting process with a closed loop harvest and transfer system on a patient, comprising:
   harvesting an amount of fat from a donor site of the patient into a collection canister;
   positioning a delivery cannula into a first portion of a grafting site of the patient;
   pumping a portion of the amount of fat directly from the collection canister into the first portion of the grafting site of the patient at a rate between 100 ml/min to 150 ml/min for at least 5 minutes;
   wherein a single piece of tubing passes through a pump used in the pumping step and connects an outlet of the collection canister to an inlet of the delivery cannula.

2. The method of claim 1 further comprising:
   delivering a second portion of the amount of fat into a second grafting site of the patient at a rate of between 100 ml/min to 150 ml/min for at least 5 minutes.

3. The method of claim 2 wherein the grafting site and the second grafting site are on a breast or the grafting site is on a right breast and the second grafting site is on a left breast.

4. The method of claim 1 further comprising:
   manipulating or treating at least a portion of the amount of fat from a harvesting step, wherein the step of manipulating or treating comprises one or more of a step of centrifuging harvested fat;
   a step of filtering harvested fat;
   a step of gravitational separation of harvested fat;
   or a step of mixing harvested fat;
   or a step of incorporating one or more substances into harvested fat helpful to ensuring viability of fat cells for the pumping process or for survival after a grafting process.

5. The method of claim 4 further comprising adapting a portion of the harvesting step or the delivering step to accommodate for a partial defect at the grafting site or to accommodate for a scarring from radiated tissue at the grafting site or to accommodate for an implant volume inadequacy at the grafting site.

6. The method of claim 1 wherein the portion of the amount of fat is 700 cc and the delivering step is less than 22 minutes.

7. The method of claim 1 wherein fat grafting process is performed as part of a breast reconstruction procedure or a cosmetic breast revision procedure or as part of a cosmetic body contouring procedure.

8. A method of performing a fat grafting process with a closed loop harvest and transfer system on a patient, comprising:
   harvesting an amount of fat from a donor site of the patient into a collection canister;
   positioning a delivery cannula into a first portion of a grafting site of the patient;
   pumping a portion of the amount of fat directly from the collection canister into the first portion of the grafting site of the patient at a rate of between 100 ml/min to 250 ml/min until a first volume of fat is indicated by a pump used during the pumping a portion step; and
   positioning the delivery cannula into a second portion of a grafting site of the patient; and
   pumping a second portion of the amount of fat directly from the collection canister into the second portion of the grafting site of the patient at a rate of between 100 ml/min to 250 ml/min until a second volume of fat is indicated by the pump used during the pumping a second portion step, wherein a single piece of tubing passes through the pump used in the pumping steps and connects an outlet of the collection canister to an inlet of the delivery cannula; and wherein total volume of fat grafted is between 200cc to 795cc and time taken to transfer the fat is between 15 minutes to 25 minutes.

9. The method of claim 8 further comprising operating the pump used in the pumping a portion steps continuously while performing the positioning the delivery cannula steps or operating the pump used in the pumping a portion step at a first flow rate during the pumping a portion step and at a second different flow rate during the pumping a second portion step.

* * * * *